US009440091B2

(12) United States Patent
Jarverud et al.

(10) Patent No.: US 9,440,091 B2
(45) Date of Patent: Sep. 13, 2016

(54) METHOD OF REDUCING THE OCCURRENCE OF ARRHYTHMIAS VIA PHOTOBIOMODULATION AND APPARATUS FOR SAME

(71) Applicant: St. Jude Medical, Atrial Fibrillation Division, Inc., St. Paul, MN (US)

(72) Inventors: Karin Jarverud, Solna (SE); Cecilia Emmanuelsson, Marsta (SE); Anders Bjorling, Solna (SE); Kjell Noren, Solna (SE)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 0 days.

(21) Appl. No.: 14/933,112

(22) Filed: Nov. 5, 2015

(65) Prior Publication Data

US 2016/0059035 A1   Mar. 3, 2016

Related U.S. Application Data

(62) Division of application No. 13/047,983, filed on Mar. 15, 2011, now Pat. No. 9,180,307.

(51) Int. Cl.
*A61N 5/06* (2006.01)
*A61N 1/39* (2006.01)
(Continued)

(52) U.S. Cl.
CPC .............. *A61N 5/0613* (2013.01); *A61N 1/362* (2013.01); *A61N 1/39* (2013.01); *A61N 5/0603* (2013.01);
(Continued)

(58) Field of Classification Search
CPC ............ A61N 1/30; A61N 1/00; A61N 1/39; A61N 5/06; A61B 18/18; A61B 5/05; A61B 5/117
USPC ......... 604/20; 600/345, 595; 606/2, 3, 7, 15; 607/23, 88, 92, 122
See application file for complete search history.

(56) References Cited

U.S. PATENT DOCUMENTS 5,800,478 A   9/1998 Chen et al.
6,156,028 A   12/2000 Prescott
(Continued)

FOREIGN PATENT DOCUMENTS

WO   2008066423   6/2008

OTHER PUBLICATIONS

Bjordal, J.M., et al., Low-Level Laser Therapy in Acute Pain: A Systematic Review of Possible Mechanisms of Action and Clinical Effects in Randomized Placebo-Controlled Trials, Photomed. and Laser Surgery, vol. 24, pp. 158-168.
(Continued)

*Primary Examiner* — William Thomson
*Assistant Examiner* — Victor Shapiro
(74) *Attorney, Agent, or Firm* — Wiley Rein LLP

(57) ABSTRACT

In response to local or systemic inflammation in a patient, photobiomodulation therapy is applied to a cardiac location to reduce the risk and/or occurrence of cardiac arrhythmia. Once inflammation is identified, photobiomodulation therapy can be applied in any suitable fashion (e.g., via a catheter- or transesophageal probe-mounted photoemitter, via an externally-applied photoemitter, or via photoemitter incorporated into an implantable medical device). Photobiomodulation therapy can also be employed to good advantage in conjunction with non-photobiomodulation therapy (e.g., traditional cardiac rhythm management therapies).

20 Claims, 3 Drawing Sheets

(51) Int. Cl.
*A61N 1/362* (2006.01)
*A61B 5/05* (2006.01)
*A61B 5/103* (2006.01)
*A61B 18/18* (2006.01)
*A61N 1/00* (2006.01)
*A61B 5/117* (2016.01)
*A61N 1/30* (2006.01)

(52) U.S. Cl.
CPC .................. *A61B 5/05* (2013.01); *A61B 5/103* (2013.01); *A61B 5/117* (2013.01); *A61B 18/18* (2013.01); *A61N 1/00* (2013.01); *A61N 1/30* (2013.01); *A61N 5/06* (2013.01); *A61N 2005/0602* (2013.01); *A61N 2005/063* (2013.01); *A61N 2005/0609* (2013.01); *A61N 2005/0612* (2013.01); *A61N 2005/0626* (2013.01)

(56) References Cited

U.S. PATENT DOCUMENTS

| | | |
|---|---|---|
| 6,502,576 B1 | 1/2003 | Lesh |
| 6,514,249 B1 | 2/2003 | Maguire et al. |
| 6,953,457 B2 | 10/2005 | Farr et al. |
| 7,596,412 B1 | 9/2009 | Kroll |
| 7,837,634 B2 | 11/2010 | Costello |
| 2002/0123674 A1 | 9/2002 | Plicchi et al. |
| 2004/0260367 A1 | 12/2004 | De Taboada et al. |
| 2006/0020045 A1 | 1/2006 | Berlin |
| 2006/0100190 A1 | 5/2006 | Cheong et al. |
| 2010/0016783 A1 | 1/2010 | Bourke et al. |
| 2010/0217367 A1 | 8/2010 | Belson |
| 2010/0233727 A1 | 9/2010 | Dudley et al. |
| 2010/0280563 A1 | 11/2010 | Norlin-Weissenrieder et al. |
| 2012/0157804 A1 | 6/2012 | Rogers et al. |

OTHER PUBLICATIONS

Boos, C.J., et al., Is Atrial Fibrillation an Inflammatory Disorder, European Heart Journal, 2006, vol. 27, pp. 136-149.

Cardin, S., et al., Evolution of the Atrial Fibrillation Substrate in Experimental Congestive Heart Failure: Angiotensin-Dependent and -Independent Pathways, Cardiovasular Research, 2003, vol. 60, pp. 315-325.

Healey, J.S., et al., Prevention of Atrial Fibrillation with Angiotensin-Converting Enzyme Inhibitors and Angiotensin Receptor Blockers, Journal of the American College of Cardiology, 2005, vol. 45, pp. 1832-1839.

Oron, U., et al., Low-Energy Laser Irradiation Reduces Formation of Scar Tissue After Myocardial Infarction in Rats and Dogs, Circulation, 2001, vol. 103, pp. 296-301.

METHOD OF REDUCING THE OCCURRENCE OF ARRHYTHMIAS VIA PHOTOBIOMODULATION AND APPARATUS FOR SAME

CROSS-REFERENCE TO RELATED APPLICATIONS

This application is a divisional of U.S. application Ser. No. 13/047,983, filed 15 Mar. 2011, now pending, which is hereby incorporated by reference in its entirety as though fully set forth herein.

BACKGROUND OF THE INVENTION a. Field of the Invention

The instant invention relates generally to the reduction and prevention of arrhythmias, such as atrial fibrillation. More specifically, the instant invention relates to apparatus and methods for reducing and preventing arrhythmias using photobiomodulation therapy, either alone or in conjunction with other therapies.

b. Background Art

In photobiomodulation therapy, laser light is applied to tissue in order to address an abnormal tissue response. In general, photobiomodulation can be described as the use of light to induce a biological response in living cells and tissue as a direct result of the absorbance of light by the living cells and tissue.

One widespread and widely accepted use of photobiomodulation therapy is for the reduction of pain. For example, photobiomodulation has been shown to reduce pain associated with acute inflammation, for example resulting from acute ankle sprains, acute Achilles tendonitis, and oral surgery. In these circumstances, photobiomodulation therapy is presumed to exert anti-inflammatory effects, for example by reducing the levels of prostaglandin $E_2$, tumor necrosis factor-$\alpha$, and interleukin-1.

It is widely accepted that some of the effects of photobiomodulation are exerted through interaction between the laser light and an enzyme, cytochrome c oxidase, present in mitochondria. This enzyme functions as a photoacceptor for light of certain wavelengths. After absorption of light, energy transfer occurs. Cytochrome c oxidase is the last enzyme in the cellular respiratory chain and is crucial for the formation of ATP which, in turn, provides energy for biochemical processes such as muscle contraction and metabolic reactions. For example, larger numbers of non-damaged mitochondria as well as higher levels of ATP have been observed in the ischemic zone after myocardial infarction in animals treated with photobiomodulation therapy as compared to untreated animals.

Atrial fibrillation is one of the most common cardiac arrhythmias, affecting millions of people worldwide. The economic stress of atrial fibrillation on the health care system is enormous, and, as the western population grows older, the number of atrial fibrillation patients is predicted to rise.

It is known that atrial fibrillation results from disorganized electrical activity in the heart muscle (the myocardium). The underlying causes of atrial fibrillation, however, are not completely understood, though it is understood that hypertensive patients are at a higher risk of developing atrial fibrillation.

It is also known that angiotensin II causes inflammation and vice versa. Further, the induction of atrial fibrosis is angiotensin II dependent, and atrial fibrosis is thought to be one of the mechanisms causing atrial fibrillation. Indeed, human atrial tissue expression of angiotensin II receptors have been linked with increased cell death and leukocyte infiltration. This may demonstrate a potential link between the renin-angiotensin-aldosterone system ("RAAS"), inflammation, and atrial fibrillation. As known, RAAS inhibition has desirable effects, both in primary and secondary prevention of atrial fibrillation.

BRIEF SUMMARY OF THE INVENTION

The inventors thus suspect that inflammation of cardiac tissue plays a role in the initiation of certain arrhythmias, such as atrial fibrillation. Photobiomodulation therapy is useful in the reduction of inflammation. Accordingly, it is an object of the present invention to prevent and reduce atrial fibrillation by addressing cardiac inflammation via the application of, inter alia, photobiomodulation therapy.

Disclosed herein is a method of reducing the occurrence of cardiac arrhythmia, including the steps of: identifying inflammation indicative of a risk of cardiac arrhythmia in a patient; and applying photobiomodulation therapy to a cardiac location in order to reduce a likelihood of a cardiac arrhythmia. The inflammation may be systemic or local and, if local, may be either local to cardiac tissue or otherwise. The photobiomodulation therapy desirably utilizes light having a wavelength between about 600 nm and about 1100 nm, and can optionally be provided in conjunction with non-photobiomodulation therapy (e.g., cardiac pacing).

The photobiomodulation therapy can be applied in a number of different ways. For example, in one aspect, a catheter having a photoemitter is navigated through a patient's vasculature to a position proximate the cardiac location and then the photoemitter is activated to deliver photobiomodulation therapy to the inflamed cardiac location.

In another aspect, a photoemitter is positioned on an exterior surface of a patient's body proximate the cardiac location and activated to deliver photobiomodulation therapy to the inflamed cardiac location.

In still another aspect, a transesophageal probe having a photoemitter is deployed to a location proximate the cardiac location via a patient's esophagus. The photoemitter is then activated to deliver photobiomodulation therapy to the inflamed cardiac location.

In yet another aspect, a medical device including a photoemitter is implanted at a location proximate the cardiac location, and the photoemitter is activated to deliver photobiomodulation therapy to the inflamed cardiac location.

Optionally, at least one physiologic characteristic is monitored, and activation of the photoemitter to deliver photobiomodulation therapy is responsive to the monitored at least one physiologic characteristic. Suitable physiologic characteristics include, but are not limited to, pressures and myocardial wall accelerations. The photoemitter may also be activated to deliver photobiomodulation therapy "on demand" (e.g., responsive to a patient's input) or according to a prescribed or preselected treatment schedule.

It is also contemplated that the implanted medical device can include, in addition to a photoemitter, a lead operable in at least one of a cardiac sensing mode and a cardiac pacing mode. In such embodiments, the activation of the photoemitter to deliver photobiomodulation therapy can be responsive to a signal received by the lead operating in a cardiac sensing mode.

Also disclosed herein is a medical device for implantation into a cardiac tissue in order to reduce occurrence of cardiac arrhythmias. The device includes a photoemitter configured to deliver photobiomodulation therapy to the cardiac tissue; and at least one of a sensor to monitor a physiologic characteristic and a therapy delivery element to deliver a non-photobiomodulation therapy to the cardiac tissue. The sensor to monitor a physiologic characteristic can be a pressure sensor, an accelerometer, or any other device suitable for use in measuring physiological characteristics.

The photoemitter can be an optical fiber coupled to a light source, a litroenergic material, or any other device suitable for delivering light of an appropriate wavelength and intensity to tissue.

The foregoing and other aspects, features, details, utilities, and advantages of the present invention will be apparent from reading the following description and claims, and from reviewing the accompanying drawings.

DETAILED DESCRIPTION OF THE INVENTION

Figure 1A:
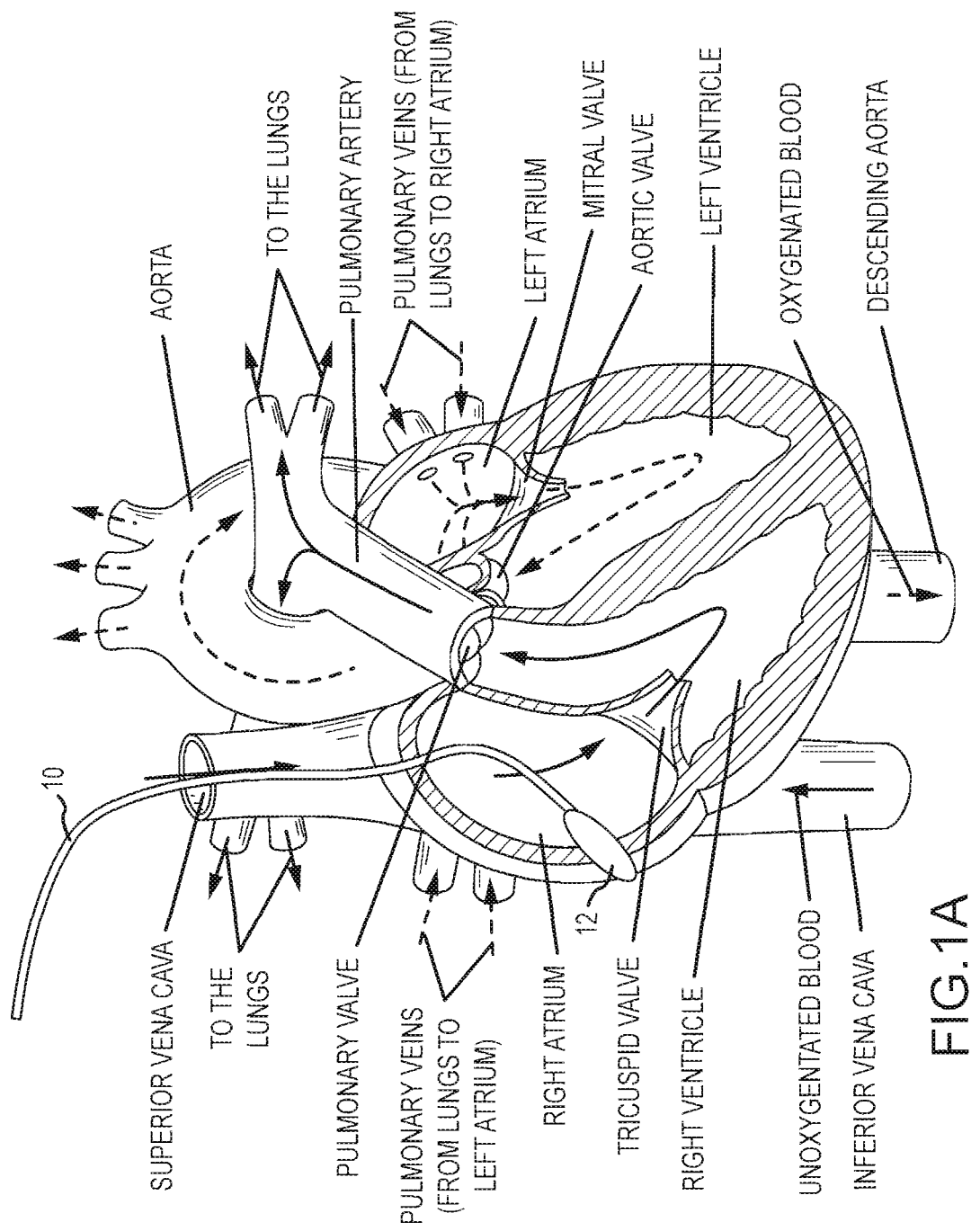
FIG. 1A illustrates a photoemitter deployed into the right atrium of a patient's heart via the patient's vasculature.

The present invention provides apparatus and methods for preventing and reducing the occurrence of cardiac arrhythmias, such as atrial fibrillation, through the application of, inter alia, photobiomodulation therapy to inflamed cardiac tissue. Though the present invention will be described in the context of preventing and reducing the occurrence of cardiac arrhythmias, it is contemplated that the teachings herein can be practiced to good advantage in other settings as well. For example, photobiomodulation therapy as described herein may also be practiced in conjunction with spinal cord stimulation, vagal nerve stimulation, gastric stimulation, or any other therapy delivered via an implantable pulse generator.

As described above, the inventors theorize that there is a link between cardiac inflammation and the risk of developing cardiac arrhythmia. Thus, methods of preventing and reducing the occurrence of cardiac arrhythmias according to the present invention include identifying inflammation that is indicative of a risk of a patient developing cardiac arrhythmia. For purposes of this disclosure, inflammation refers not only to local inflammation, but also to systemic inflammation.

As described above, there is a relationship between angiotensin II and inflammation. Thus, when there is a systemic inflammatory state in a subject, there may also be increased levels of angiotensin II in the blood. Because angiotensin II acts as a pro-inflammatory molecule, the increased level of angiotensin may, in turn, lead to local inflammation in cardiac tissue, thus increasing the risk of atrial fibrosis and atrial fibrillation. In other words, whether inflammation is systemic or local (to the heart or otherwise), the increased levels of angiotensin II will cause an increased risk for AF.

Systemic inflammation can be detected in various ways, such as through analysis of body temperature, blood samples, and IEGM. For example, the following blood markers often indicate systemic inflammation: c-reactive protein (CRP), interleukin-6 (IL-6), tumor necrosis factor-alpha (TNF-α) and erythrocyte sedimentation rate. Similarly, Troponin T, troponin I, creatine kinase MB (CK-MB), and myoglobin are markers of myocardial damage, while cystatin C is a marker of renal damage, which may occur at inflammation. In addition, angiotensin-converting enzyme can be measured in blood as a marker of increased angiotensin II activity.

Once inflammation (systemic or local, to the heart or otherwise) has been identified, photobiomodulation therapy can be applied in order to reduce local inflammation in cardiac tissue (e.g., ischemic ventricular regions, infarct ventricular regions). This, in turn, reduces the patient's risk of developing an arrhythmia.

The present invention encompasses any number of methodologies of delivering photobiomodulation therapy to an inflamed cardiac location, which will be familiar to those of ordinary skill in the art. For example, United States patent application publication no. 2004/0260367, which is hereby incorporated by reference as though fully set forth herein, discloses delivery of photobiomodulation to a patient's heart via an externally-applied device (in FIGS. 2A and 2B), via a catheter (in FIG. 12), and via a transesophageal probe (in FIGS. 11A and 11B). Similarly, PCT publication WO2008066423, which is hereby incorporated by reference as though fully set forth herein, discloses an implantable cardiac device that can also deliver phototherapy in order to facilitate the healing process associated with device implantation.

Neither United States patent application publication no. 2004/0260367 nor PCT publication WO2008066423, however, recognizes the beneficial, arrhythmia-reducing and arrhythmia-preventing effects of photobiomodulation therapy. Nonetheless, because various suitable methods of delivering photobiomodulation therapy will be familiar to those of ordinary skill in the art, these methodologies will only be described herein to the extent necessary to understand the present invention.

Figure 1B:
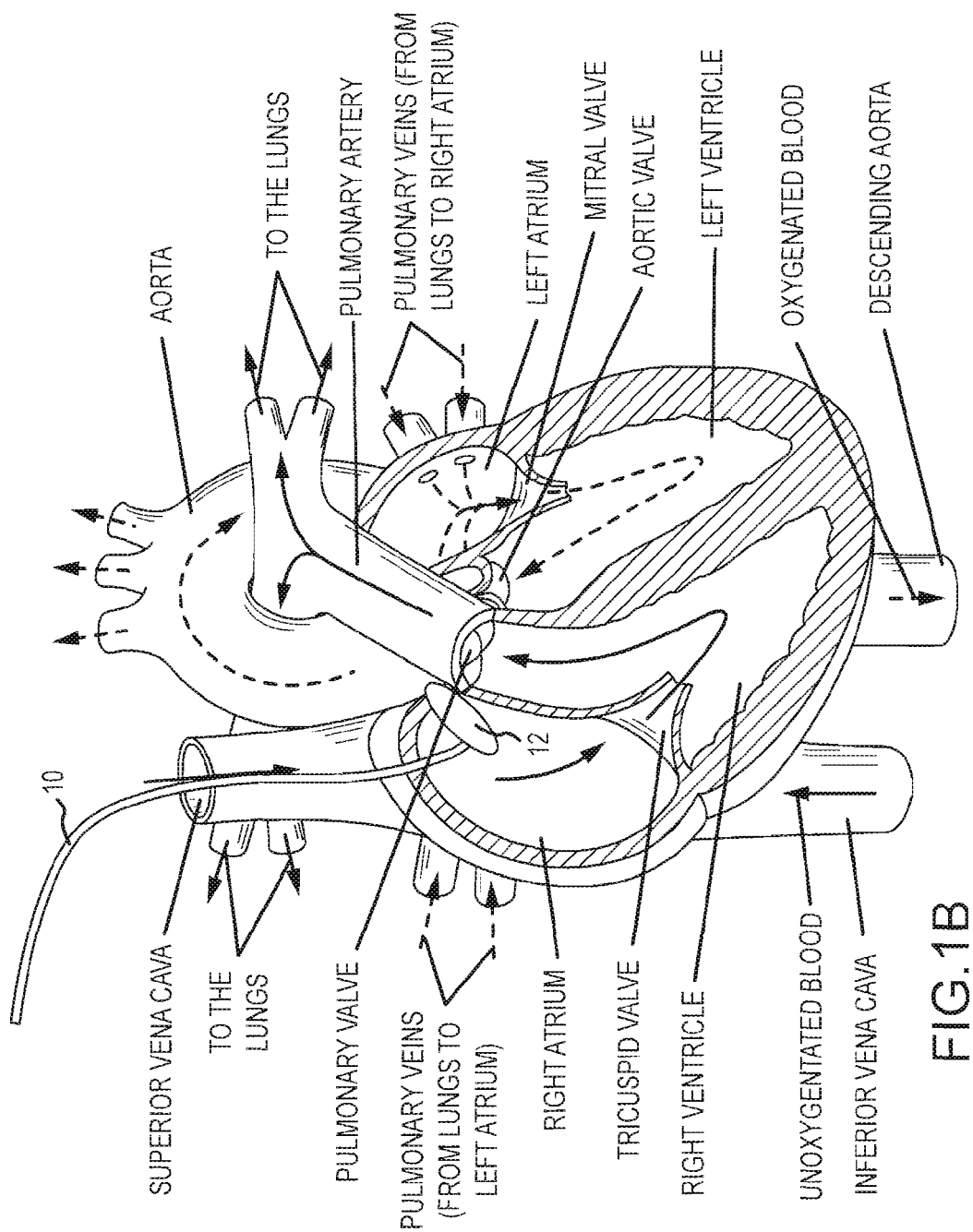
FIG. 1B also illustrates a photoemitter deployed into the right atrium of a patient's heart via the patient's vasculature.

FIGS. 1A and 1B illustrate a first method of delivering photobiomodulation therapy to an inflamed cardiac location. As shown in FIGS. 1A and 1B, a catheter 10 having a photoemitter 12 at a distal end thereof is navigated through the patient's vasculature to a position proximate the inflamed cardiac location. For the sake of illustration, catheter 10 is shown as being introduced into the patient's right atrium via the superior vena cava. It should be understood, of course, that catheter 10 may be navigated through the patient's vasculature, using any suitable known technique (e.g., steerable catheters, non-steerable catheters introduced through steerable introducer sheaths, catheters introduced over guidewires, and the like), into any cardiac chamber without departing from the spirit and scope of the present invention.

Figure 2:
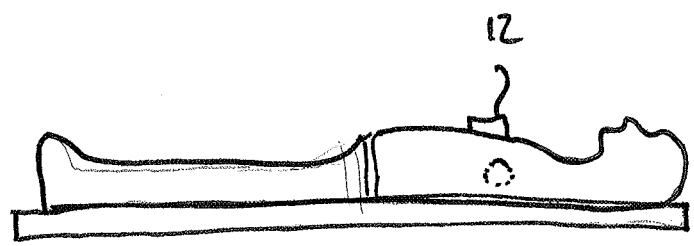
FIG. 2 depicts a photoemitter for the external application of photobiomodulation therapy.

FIG. 2 depicts a second method of delivering photobiomodulation therapy to an inflamed cardiac location. As shown in FIG. 2, a photoemitter 12 is positioned on an exterior surface of the patient's body proximate the inflamed cardiac location and activated to emit light, thereby delivering photobiomodulation therapy to the inflamed cardiac location. Such externally-applied photobiomodulation therapy has the advantage of being completely non-invasive, but may not be as effective as internally-applied (e.g., catheter-delivered) photobiomodulation therapy. In addition, though FIG. 2 depicts the patient on an examination table, it should be understood that photoemitter 12 may be provided as part of or on a belt or other wearable device that permits the patient to stand, and even move about, while undergoing photobiomodulation therapy.

Figure 3:
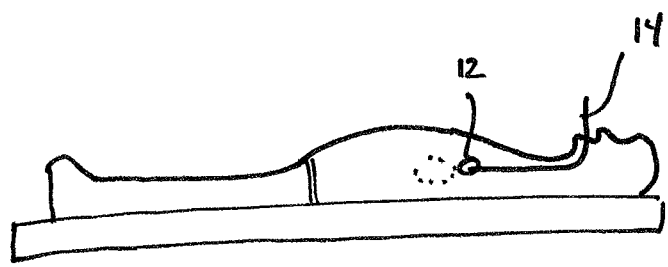
FIG. 3 depicts a photoemitter deployed transesophageally.

FIG. 3 depicts a third method of delivering photobiomodulation therapy to an inflamed cardiac location. As shown in FIG. 3, a photoemitter 12 is positioned on a transesophageal probe 14. Probe 14 is introduced, via the patient's esophagus, to a location proximate the inflamed cardiac location, and photoemitter 12 is activated to deliver photobiomodulation therapy thereto. One of ordinary skill in the art will appreciate that this method of delivering photobiomodulation therapy is slightly less invasive than catheter-delivered photobiomodulation therapy and likely to be more effective than externally-applied photobiomodulation therapy.

Photoemitter 12 may include any suitable light source, as generally known in the photobiomodulation art. For example, in some embodiments of the invention, photoemitter 12 includes one or more optical fibers coupled to one or more light sources. In the embodiment of the invention depicted in FIGS. 1A and 1B, the optical fibers (and any lenses used in connection therewith) are connected to catheter 10 so as to be carried by catheter 10 through the patient's vasculature. Likewise, in the embodiment of the invention depicted in FIG. 3, the optical fibers (and any lenses used in connection therewith) are connected to probe 14 so as to be carried by probe 14 through the patient's esophagus. Typically, the light source will remain outside the patient's body, but it is within the scope of the invention to provide a light source that is sufficiently small to be incorporated into catheter 10 or probe 14 along with the optical fiber assembly.

In other embodiments of the invention, photoemitter 12 may include a litroenergic material. Litroenergic materials are materials that emit light continuously without an external power source. Suitable litroenergic materials include LITROSPHERES™, manufactured by MPK Co. of Clayton, Wis. Such materials can be molded into and/or painted onto the distal end of catheter 10, probe 14, or another suitable device.

Typically, the light used in photobiomodulation therapy delivered according to the teachings herein will have a wavelength of between about 600 nm and about 1100 nm. Of course, these wavelengths are merely exemplary, and other wavelengths could be employed, if deemed beneficial to the patient, without departing from the spirit and scope of the present invention.

In some embodiments of the invention, one or more medical devices respectively including one or more photoemitters are implanted into a patient at locations proximate inflamed cardiac locations. Methods of implantation of such medical devices are generally known, for example in connection with the implantation of cardiac pacing leads.

An implanted photoemitter can be activated as necessary or desirable in order to prevent and reduce the occurrence of cardiac arrhythmia, without necessitating a catheterization procedure every time photobiomodulation therapy is to be delivered. Photoemitter implantation may be desirable where a preselected treatment schedule calls for photobiomodulation therapy to be delivered over an extended period of time, such as every other day for two weeks.

Photoemitter implantation may also be advantageous where photobiomodulation therapy is delivered "on demand" by the patient. For example, if the patient experiences symptoms of hypertension, which may be a precursor to cardiac arrhythmia, the patient can activate the photoemitter in order to reduce or prevent the occurrence of an arrhythmia, similar to how a patient might take a nitroglycerin pill when experiencing symptoms of angina.

It is also contemplated to incorporate one or more photoemitters into an implantable cardiac pacing lead, such as a cardiac resynchronization therapy (CRT), cardiac resynchronization therapy defibrillator (CRT-D), implantable cardioverter-defibrillator (ICD), or brady device. Such a configuration advantageously provides a single device capable of delivering both traditional cardiac rhythm management therapy and photobiomodulation therapy.

An implanted medical device including a photoemitter may additionally, or alternatively, include a sensor (e.g., a sensing lead) to enable monitoring of one or more physiologic characteristics. A control system can be established that activates the photoemitter in response to the monitored physiologic characteristics.

As one example, the photoemitter can be coupled to a pressure sensor, such as the HeartPOD™ implantable heart failure therapy system, which measures a patient's left atrial pressure. As another example, the photoemitter can be coupled to a sensor that measures atrial wall stress. As yet another example, the photoemitter can be coupled to an accelerometer that measures the acceleration of the atrial wall. Other suitable sensors include motion sensors, position sensors, and sensors for measuring cardiac electrograms.

The control system can, in response to measurements made by the sensor or sensors, activate the photoemitter as appropriate in order to prevent or reduce the occurrence of a cardiac arrhythmia. For example, in the case where the sensor measures cardiac electrograms, the control system can activate the photoemitter when an irregular electrogram is detected.

Although several embodiments of this invention have been described above with a certain degree of particularity, those skilled in the art could make numerous alterations to the disclosed embodiments without departing from the spirit or scope of this invention. For example, one of ordinary skill in the art will readily appreciate that photobiomodulation therapy can be delivered according to any suitable schedule using any suitable wavelength of light.

As another example, it should be understood that sensors used as part of a control system for the delivery of photobiomodulation therapy need not be implanted, and may be external to the patient. For example, rather than using an internal cardiac sensing lead, the photoemitter may be coupled to the output of a Holter monitor.

As still another example, the non-photobiomodulation therapy is not limited to traditional cardiac rhythm management therapy, and includes, for example, pharmacologic therapy, ablation therapy, surgical therapies, and the like.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical device for implantation into a cardiac tissue in order to reduce occurrence of cardiac arrhythmias comprising:
   a photoemitter configured to deliver photobiomodulation therapy to a locally inflamed cardiac tissue in order to inhibit the development of cardiac arrhythmia by reducing inflammation of the cardiac tissue; and
   at least one of a sensor to monitor a physiologic characteristic and a therapy delivery element to deliver a non-photobiomodulation therapy to the cardiac tissue.

2. The medical device according to claim 1, wherein the sensor to monitor a physiologic characteristic comprises a pressure sensor.

3. The medical device according to claim 1, wherein the sensor to monitor a physiologic characteristic comprises an accelerometer.

4. The medical device according to claim 1, wherein the photoemitter comprises an optical fiber coupled to a light source.

5. The implant according to claim 1, wherein the photoemitter comprises a litroenergic material.

6. The implant according to claim 1, wherein the sensor to monitor a physiologic characteristic comprises a motion sensor.

7. The implant according to claim 1, wherein the sensor to monitor a physiologic characteristic comprises a sensor for measuring cardiac electrograms.

8. The implant according to claim 1, further comprising a control system, and wherein the control system is configured:
   to receive an input from the sensor;
   to detect, from the input, a physiologic condition indicative of a developing cardiac arrhythmia; and
   to activate the photoemitter to deliver photobiomodulation therapy to the cardiac tissue to mitigate the physiologic condition indicative of the developing cardiac arrhythmia.

9. An apparatus for preventing a cardiac arrhythmia from developing in a patient, comprising:
   a sensor to monitor a physiologic characteristic;
   a photoemitter; and
   a control system that receives an output of the sensor as an input and that is configured to activate the photoemitter to deliver photobiomodulation therapy to the cardiac tissue in response to the output of the sensor.

10. The apparatus according to claim 9, further comprising a medical implant, and wherein the photoemitter is carried by the medical implant.

11. The apparatus according to claim 9, wherein the photoemitter comprises a litroenergic material.

12. The apparatus according to claim 9, wherein the sensor comprises one or more of a pressure sensor, an atrial wall stress sensor, an accelerometer, a motion sensor, a position sensor, and a sensor that measures cardiac electrograms.

13. The apparatus according to claim 9, further comprising a therapy delivery element to deliver a non-photobiomodulation therapy to the cardiac tissue.

14. The apparatus according to claim 13, wherein the therapy delivery element comprises a device for cardiac rhythm management.

15. The apparatus according to claim 9, wherein the photoemitter is further configured for on demand activation by a patient.

16. The apparatus according to claim 9, further comprising a catheter, and wherein the photoemitter is mounted to the catheter.

17. The apparatus according to claim 9, further comprising a transesophageal probe, and wherein the photoemitter is mounted to the transesophageal probe.

18. The apparatus according to claim 9, wherein the photoemitter is configured to be applied to an exterior of a patient's body.

19. An apparatus for preventing a cardiac arrhythmia from developing in a patient, comprising:
   a sensor configured to detect a physiologic condition indicative of a risk of the patient developing a cardiac arrhythmia;
   a photoemitter configured to apply photobiomodulation therapy to a cardiac tissue in order to inhibit the development of the cardiac arrhythmia by reducing inflammation of the cardiac tissue; and
   a control system configured to activate the photoemitter to deliver the photobiomodulation therapy to the cardiac tissue responsive to an output of the sensor.

20. The apparatus according to claim 19, wherein the physiologic condition indicative of a risk of the patient developing a cardiac arrhythmia comprises tissue inflammation.

* * * * *